(12) United States Patent
Kasaba et al.

(10) Patent No.: US 11,319,139 B2
(45) Date of Patent: May 3, 2022

(54) INJECTOR

(71) Applicant: KABUSHIKI KAISHA SHOFU, Kyoto (JP)

(72) Inventors: Hideto Kasaba, Kyoto (JP); Hiroyuki Kobayashi, Kyoto (JP); Hiroyuki Shioi, Kyoto (JP); Hiroshi Yaana, Kyoto (JP); Toshiyuki Nakatsuka, Kyoto (JP); Yukihiro Ogawa, Ibaraki (JP); Hisako Tokura, Ibaraki (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 0 days.

(21) Appl. No.: 16/445,299

(22) Filed: Jun. 19, 2019

(65) Prior Publication Data

US 2019/0389646 A1    Dec. 26, 2019

(30) Foreign Application Priority Data

Jun. 21, 2018  (JP) .............................. JP2018-118258

(51) Int. Cl.
*B65D 83/00*    (2006.01)

(52) U.S. Cl.
CPC ................................ *B65D 83/0005* (2013.01)

(58) Field of Classification Search
CPC .... B65D 83/0005; A61M 2005/31056; A61M 2005/3158; A61M 2005/3139; A61M 2005/3131; A56M 5/3135; A56M 5/178; A56M 5/31; A61C 5/00
USPC .................. 222/386; 604/110, 118, 218, 220
See application file for complete search history.

(56) References Cited

U.S. PATENT DOCUMENTS

| | | | | |
|---|---|---|---|---|
| 4,391,272 A | * | 7/1983 | Staempfli | A61M 5/508 604/110 |
| 4,758,232 A | * | 7/1988 | Chak | A61B 5/15003 600/578 |
| 4,781,684 A | * | 11/1988 | Trenner | A61M 5/5013 604/110 |
| 4,826,484 A | * | 5/1989 | Haber | A61M 5/315 604/110 |
| 5,037,393 A | * | 8/1991 | Ellgass | A61M 5/348 604/110 |

(Continued)

FOREIGN PATENT DOCUMENTS

| | | |
|---|---|---|
| CA | 2 329 707 | 11/1999 |
| CN | 1030188 | 1/1989 |

(Continued)

OTHER PUBLICATIONS

Extended European Search Report dated Sep. 10, 2019 in corresponding European Patent Application No. 19181122.3.

(Continued)

*Primary Examiner* — Lien M Ngo
(74) *Attorney, Agent, or Firm* — Wenderoth, Lind & Ponack, L.L.P.

(57) ABSTRACT

An injector comprises a cylindrical barrel including a discharge port, a seal body coming into close contact with an inner circumferential surface of the barrel, a plunger for pushing and moving the seal body to the discharge port side of the barrel, and a stopper disposed on one of the barrel and the plunger and coming into elastic contact with the other in a radial direction of the barrel.

12 Claims, 14 Drawing Sheets

(56) References Cited

U.S. PATENT DOCUMENTS

| | | | | |
|---|---|---|---|---|
| 5,047,017 | A * | 9/1991 | Koska | A61M 5/5066 604/110 |
| 5,106,372 | A * | 4/1992 | Ranford | A61M 5/5013 604/110 |
| 5,370,620 | A * | 12/1994 | Shonfeld | A61M 5/315 604/110 |
| 5,380,295 | A | 1/1995 | Vacca | |
| 6,872,191 | B2 * | 3/2005 | Lo | A61M 5/5013 604/110 |
| 8,066,668 | B2 * | 11/2011 | Wayman | A61M 5/502 604/110 |
| 9,545,464 | B2 * | 1/2017 | Roche | A61M 1/67 |
| 2005/0267410 | A1 * | 12/2005 | Koska | A61M 5/3272 604/110 |
| 2006/0173411 | A1 * | 8/2006 | Barere | A61M 5/5013 604/110 |
| 2008/0275387 | A1 | 11/2008 | Yeadon et al. | |
| 2012/0232492 | A1 | 9/2012 | Hato | |
| 2015/0105754 | A1 | 4/2015 | Roche et al. | |
| 2017/0182254 | A1 * | 6/2017 | Heinsbergen | A61M 5/31511 |
| 2018/0296766 | A1 | 10/2018 | Kakuta | |

FOREIGN PATENT DOCUMENTS

| | | |
|---|---|---|
| JP | 08-504352 | 5/1996 |
| JP | 9-253205 | 9/1997 |
| JP | 2002-515268 | 5/2002 |
| JP | 5090555 | 12/2012 |
| JP | 5393660 | 1/2014 |
| JP | 6091514 | 3/2017 |
| WO | 99/55402 | 11/1999 |
| WO | 2008/154630 | 12/2008 |
| WO | 2013/070663 | 5/2013 |
| WO | 2017/072992 | 5/2017 |

OTHER PUBLICATIONS

Office Action dated Dec. 24, 2021 in corresponding Chinese Application No. 201910536183.1 with English translation.
Notice of Reasons for Refusal dated Jan. 5, 2022 in corresponding Japanese Application No. 2018-118258 with English translation.
Communication pursuant to Article 94(3) EPC dated Feb. 2, 2022 in corresponding European Patent Application No. 19 181 122.3.

* cited by examiner

INJECTOR

TECHNICAL FIELD

The present invention relates to an injector.

BACKGROUND ART

An injector is conventionally known that has a configuration in which a plunger for pushing and moving a seal body toward a discharge port of a barrel is prevented from coming off from the barrel. For example, in the case of the injector described in Patent Document 1, the barrel includes a convex portion projecting from an inner circumferential surface thereof, and the plunger includes a locking portion locked to the convex portion.

PRIOR ART DOCUMENT

Patent Document

Patent Document 1: Japanese Unexamined Patent Application Publication (Translation of PCT Application) No. 2002-515268

SUMMARY OF THE INVENTION

Problem to be Solved by the Invention

However, in the case of the injector described in Patent Document 1, the seal body climbs over the convex portion projecting from the inner circumferential surface of the barrel before being housed into the barrel. In this case, the seal body may be damaged due to contact with the convex portion.

Therefore, a problem to be solved by the present invention is to house a seal body into a barrel without damage and to prevent a plunger from falling off from the barrel in an injector.

Means for Solving Problem

To solve the problem described above, an aspect of the present disclosure provides
an injector comprising:
a cylindrical barrel including a discharge port;
a seal body coming into close contact with an inner circumferential surface of the barrel;
a plunger for pushing and moving the seal body to the discharge port side of the barrel; and
a stopper disposed on one of the barrel and the plunger and coming into elastic contact with the other in a radial direction of the barrel.

Effect of the Invention

According to the present invention, the seal body can be housed into the barrel without damage and the plunger can be prevented from falling off from the barrel in the injector.

MODES FOR CARRYING OUT THE INVENTION

An injector according to an embodiment of the present invention comprises a cylindrical barrel including a discharge port, a seal body coming into close contact with an inner circumferential surface of the barrel, a plunger for pushing and moving the seal body to the discharge port side of the barrel, and a stopper disposed on one of the barrel and the plunger and coming into elastic contact with the other in a radial direction of the barrel.

According to this aspect, the seal body can be housed into the barrel without damage and the plunger can be prevented from falling off from the barrel in the injector.

The stopper may be a plate spring-shaped member including a fixed end attached to the plunger and a free end coming into elastic contact with the inner circumferential surface of the barrel.

In the stopper, the free end may be located on the base end side of the barrel with respect to the fixed end.

In the stopper, the free end may be located on the leading end side of the barrel with respect to the fixed end.

The inner circumferential surface of the barrel may be provided with a circumferential groove with which the free end of the stopper is engaged. Since the free end of the stopper engages with the circumferential groove, the plunger is prevented from coming off from the barrel.

The circumferential groove may have a slope surface extending from a bottom potion of the circumferential groove toward the leading end of the barrel and sloping with respect to the inner circumferential surface. As a result, the plunger can smoothly be housed into the barrel without the free end of the stopper being caught in the circumferential groove.

The stopper and the plunger may be integrated as one part.

The stopper may be a plate spring-shaped member including a fixed end attached to the barrel and a free end coming into elastic contact with the plunger.

The barrel may have two slits formed to extend from a base end thereof, and wherein the stopper may be made up of a portion of the barrel interposed between the two slits.

The seal body and the plunger may be integrated as one part.

Embodiments of the present invention will now be described with reference to the drawings.

First Embodiment

Figure 1:
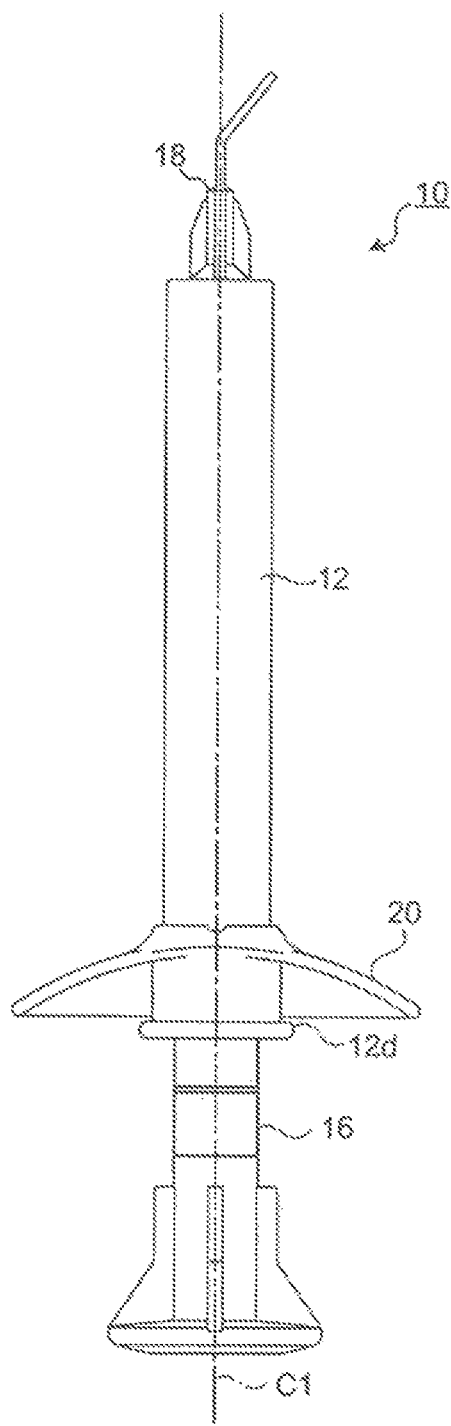
FIG. 1 is an external view of an injector according to a first embodiment of the present invention.
Figure 2:
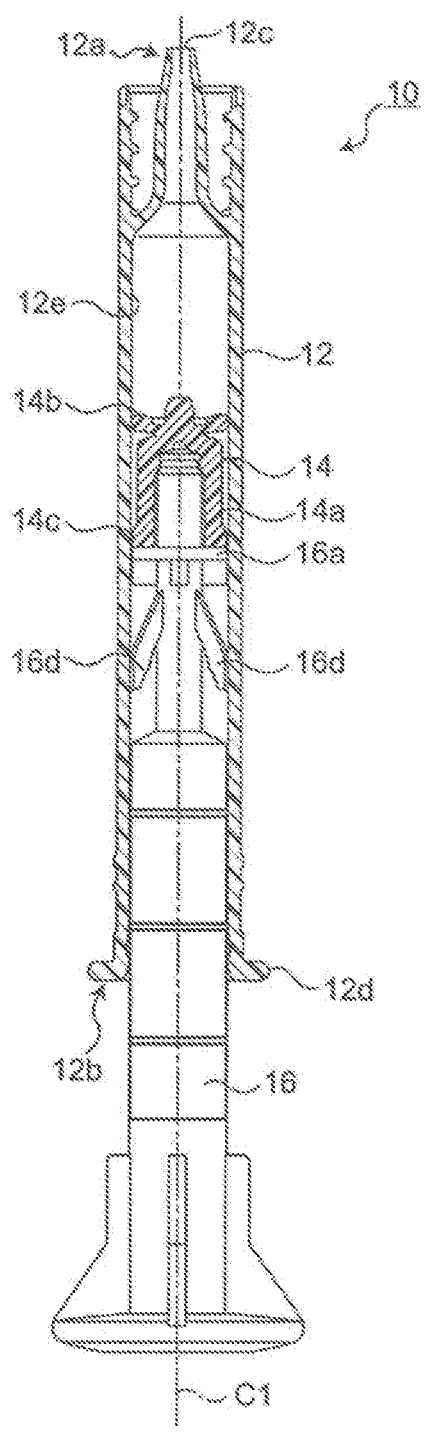
FIG. 2 is a partial cross-sectional view of the injector according to the first embodiment.

FIG. 1 is an external view of an injector according to a first embodiment of the present invention, and FIG. 2 is a partial cross-sectional view of the injector.

As shown in FIGS. 1 and 2, an injector 10 includes a barrel 12 containing, for example, a pasty fluid, a movable body 14 movably housed in the barrel 12, and a plunger 16 for pushing and moving the movable body 14. The injector 10 also has a nozzle tip 18 attached to a leading end 12a of the barrel 12 and a finger grip 20 rotatably fitted to a base end 12b of the barrel 12.

Figure 3:
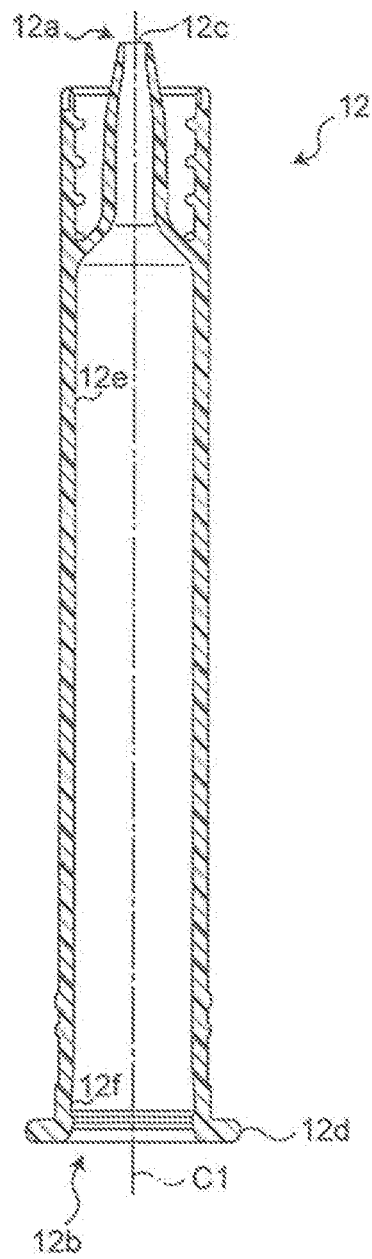
FIG. 3 is a cross-sectional view of a barrel in the injector according to the first embodiment.
Figure 4:
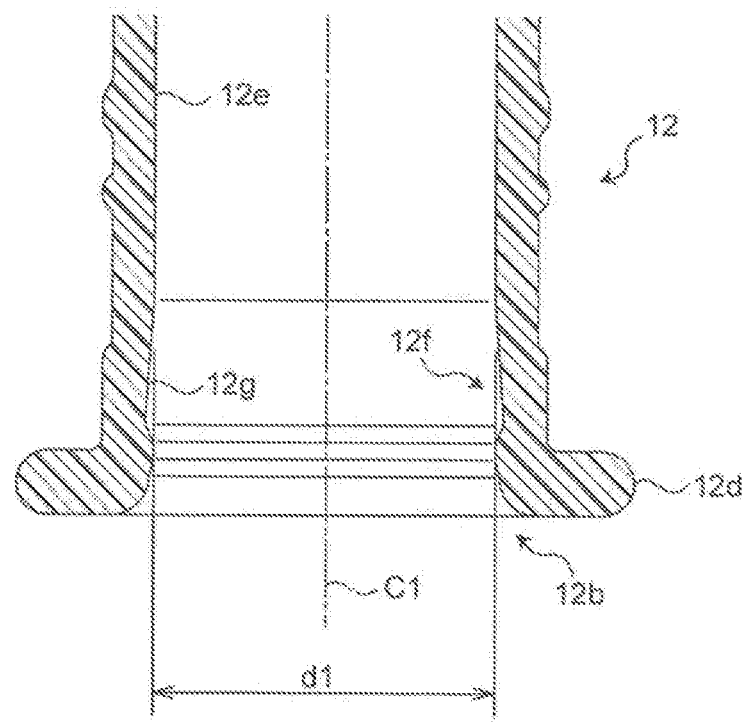
FIG. 4 is an enlarged cross-sectional view of the barrel shown in FIG. 3.

FIG. 3 is a cross-sectional view of the barrel, and FIG. 4 is an enlarged cross-sectional view of the barrel shown in FIG. 3.

As shown in FIG. 3, the barrel 12 is a cylindrical member having a central axis C1, and is made of a resin material, for example. The barrel 12 includes a discharge port 12c at the leading end 12a and a flange portion 12d at the base end 12b. By attaching the nozzle tip 18 to the leading end 12a of the barrel 12, the discharge port 12c is connected to a nozzle inside flow passage communicating with the outside in the nozzle tip 18. The flange portion 12d functions as a stopper preventing the finger grip 20 rotatably fitted to a base end side portion of the barrel 12 from falling off.

As shown in FIG. 4, a circumferential groove 12f is formed in a base end side portion of an inner circumferential surface 12e of the barrel 12. The reason why the circumferential groove 12f is formed will be described later.

Figure 5:
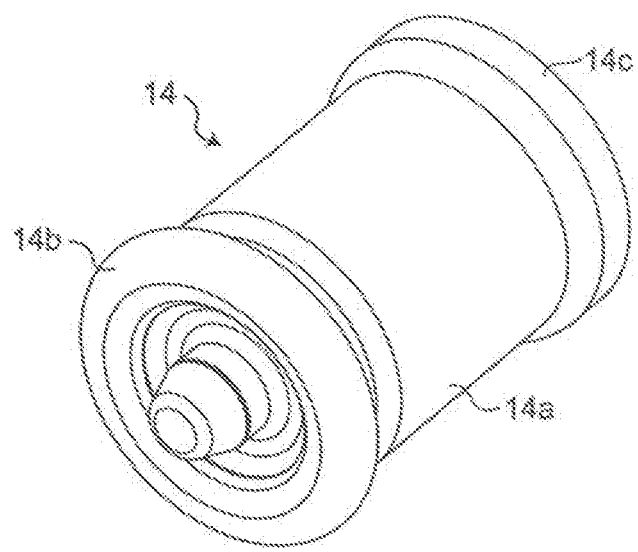
FIG. 5 is a perspective view of a movable body in the injector according to the first embodiment.
Figure 6:
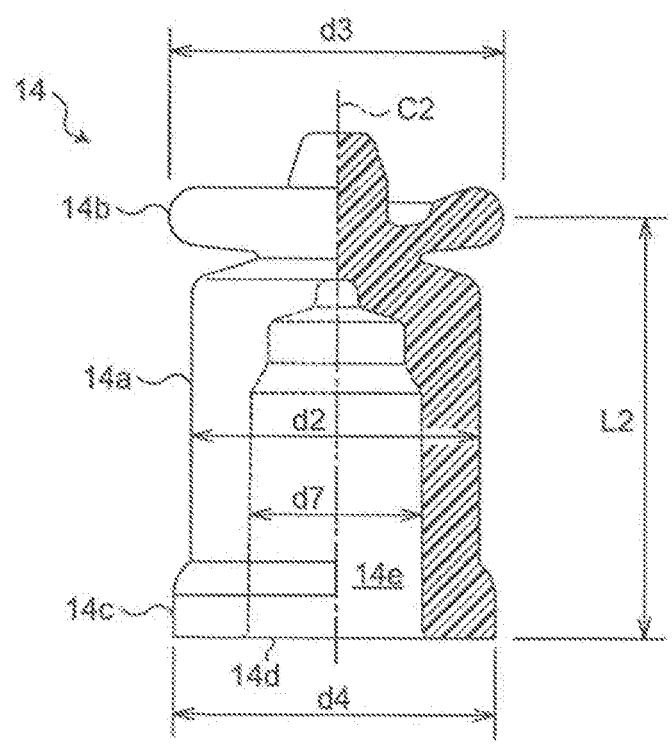
FIG. 6 is a partial cross-sectional view of the movable body shown in FIG. 5.

FIG. 5 is a perspective view of the movable body, and FIG. 6 is a partial cross-sectional view of the movable body.

As shown in FIG. 5, the movable body 14 is a substantially cylindrical member having a central axis C2. The movable body 14 is made of an elastically deformable resin material, for example. Specifically, the movable body 14 is made of a material easily elastically deformed as compared to the barrel 12.

The movable body 14 includes a main body 14a, a seal body 14b disposed on the main body 14a, and a flange 14c disposed on the main body 14a.

The main body 14a of the movable body 14 is cylindrical and has an outer diameter d2 smaller than an inner diameter d1 of the barrel 12 shown in FIG. 4. Therefore, while the movable body 14 is housed in the barrel 12, a clearance is generated between the main body 14a and the inner circumferential surface 12e of the barrel 12.

The seal body 14b of the movable body 14 has a disk shape and has an outer circumferential end brought into close contact with the inner circumferential surface 12e of the barrel 12 in a slidable and fluid-tight manner. Although the seal body 14b and the main body 14a are integrated as one part, the seal body 14b and the main body 14a may be separate parts.

For close contact of the outer circumferential end with the inner circumferential surface 12e of the barrel 12 in a fluid-tight manner, the seal body 14b has an outer diameter d3 larger than the inner diameter d1 of the barrel 12. The outer diameter d3 of the seal body 14b is larger than the outer diameter d2 of the main body 14a of the movable body 14.

Additionally, the seal body 14b has a central portion attached to a front end of the main body 14a (the end closer to the leading end 12a of the barrel 12). Additionally, an outer circumferential side portion of the seal body 14b is away from the main body 14a when the portion is in a free state (when the movable body 14 is present outside the barrel 12).

The flange 14c of the movable body 14 is a projecting portion projecting from the main body toward the inner circumferential surface of the barrel 12 and is disposed at a rear end of the main body 14a (the end closer to the base end 12b of the barrel 12). The flange 14c has an outer diameter d4 smaller than the outer diameter d3 of the seal body 14b. In the case of the first embodiment, the outer diameter d4 of the flange 14c is smaller than the inner diameter d1 of the barrel 12 and larger than the outer diameter d2 of the main body 14a. The reason why the flange 14c as described above is disposed on the movable body 14 will be described later.

For separable contact with the plunger 16, the movable body 14 also includes a planar-shaped rear end surface 14d orthogonal to the central axis C2 and includes a non-penetrating hole-shaped guide hole 14e in the rear end surface 14d.

Figure 7:
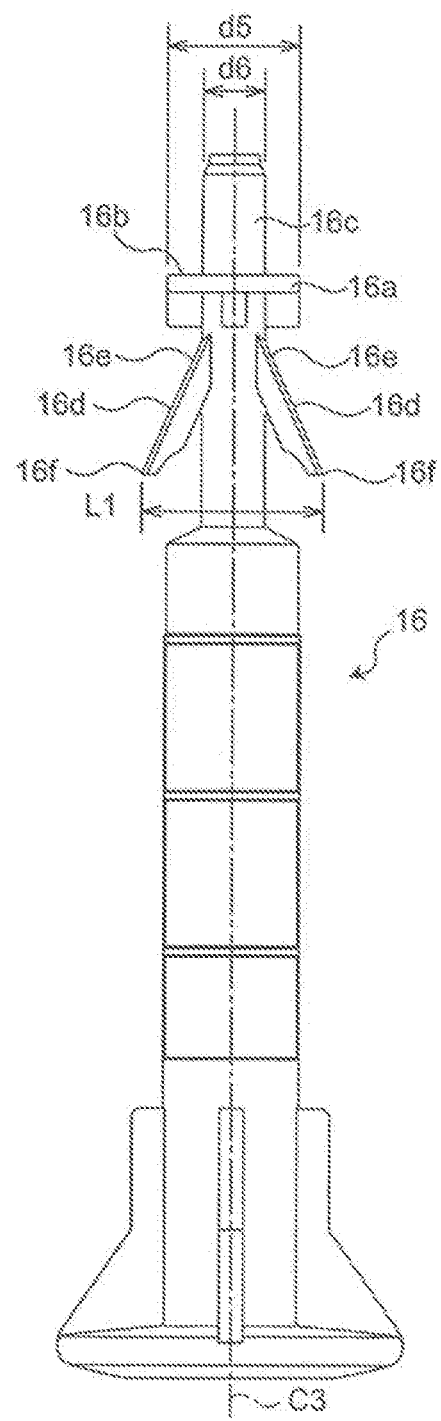
FIG. 7 is an external view of a plunger in the injector according to the first embodiment.

FIG. 7 is an external view of the plunger.

As shown in FIG. 7, the plunger 16 is a member for pushing and moving the movable body 14 housed in the barrel 12 toward the leading end 12a (i.e., the discharge port 12c) of the barrel 12, has a central axis C3, and is made of a resin material, for example. The plunger 16 is configured to come into separable contact with the movable body 14.

Specifically, the plunger 16 includes a contact portion 16a coming into contact with the movable body 14 on the front end side (the side closer to the leading end 12a of the barrel 12). The contact portion 16a has an outer diameter d5 smaller than the inner diameter d1 of the barrel 12. The contact portion 16a includes a planar-shaped contact surface 16b coming into surface contact with the planar-shaped rear end surface 14d of the movable body 14.

The plunger 16 includes a guide pin 16c projecting from the contact surface 16b of the contact portion 16a. While the rear end surface 14d of the movable body 14 is in surface contact with the contact surface 16b of the plunger 16, the guide pin 16c is received in the guide hole 14e of the movable body 14. An outer diameter d6 of the guide pin 16c is smaller than an inner diameter d7 of the guide hole 14e shown in FIG. 6 so that the guide pin is received in the guide hole 14e of the movable body 14 in a manner enabling forward and backward movement. Since the guide pin 16c is guided by the guide hole 14e, the contact surface 16b of the plunger 16 can appropriately come into surface contact with the rear end surface 14d of the movable body 14. Specifically, the movable body 14 and the plunger 16 can come into contact with each other in a state in which the central axis C2 of the movable body 14 and the central axis C3 of the plunger 16 are arranged substantially on the same straight line. As a result, the plunger 16 can push and move the movable body 14 toward the leading end 12a of the barrel 12 without tilting.

According to the plunger 16 as described above, the movable body 14 can be pushed and moved toward the leading end 12a of the barrel 12 by advancing the plunger 16. Additionally, the movable body 14 and the plunger 16 can be separated from each other by simply retracting the plunger 16.

Since the plunger 16 is not fixed to the movable body 14 while the seal body 14b is in close contact with the inner circumferential surface 12e of the barrel 12, the plunger 16 possibly comes off from the barrel 12. For example, if the injector 10 is in a state with the nozzle tip 18 located downward and a user grasps only the plunger 16 to lift the injector 10, the barrel 12 may fall off from the plunger 16 due to its own weight.

To prevent the plunger 16 from coming off from the barrel 12 in this way, stoppers 16d are disposed on the plunger 16 as shown in FIG. 7.

In the case of the first embodiment, the two stoppers 16d are disposed oppositely to each other across the central axis C3 of the plunger 16. Each of the two stoppers 16d is an elastically-deformable plate spring-shaped member including a fixed end 16e attached to the plunger 16 and a free end 16f displaceable in a radial direction of the barrel 12 (a direction orthogonal to the central axis C1 of the barrel 12). In the case of the first embodiment, the stoppers 16d and the plunger 16 are integrated as one part.

In the case of the first embodiment, the free end 16f of the stopper 16d is located on the base end 12b side of the barrel 12 with respect to the fixed end 16e. The free end 16f is farther than the fixed end 16e from the central axis C3 of the plunger 16. Therefore, the stopper 16d extends from the leading end 12a side to the base end 12b side of the barrel 12 and toward the inner circumferential surface 12e of the barrel 12.

As shown in FIG. 7, a distance L1 between the free ends 16f of the two stoppers 16d is larger than the inner diameter d1 of the barrel 12 when the free ends are in a free state (when the plunger 16 is present outside the barrel 12). Therefore, when the stoppers 16d of the plunger 16 are located inside the barrel 12, each of the two stoppers 16d is elastically deformed by the inner circumferential surface 12e of the barrel 12 such that the free ends 16f come closer to each other. This brings the free ends 16f of the stopper 16d into elastic contact with the inner circumferential surface 12e of the barrel 12 in the radial direction of the barrel 12. As a result, a friction force is generated between the barrel 12 and the free ends 16f of the stopper 16d, and the plunger 16 is restrained from coming off from the barrel 12. The term "elastic contact" as used herein means that a portion of an object during elastic deformation is in contact with another object in a restoring direction in which the object is restored to an original shape.

An elastic force of the stoppers 16d, i.e., the friction force between the inner circumferential surface 12e of the barrel 12 and the free ends 16f of the stoppers 16d, is at a level preventing the barrel 12 from coming off when a user grasps only the plunger 16 of the injector 10 in a posture with the nozzle tip 18 located downward, or at a level preventing the plunger 16 from coming off when a user grasps only the barrel 12 of the injector 10 in a posture with the nozzle tip 18 located upward. Additionally, this elastic force (i.e., friction force) is at a level allowing the user to push and move the plunger 16 toward the leading end 12a of the barrel 12. To achieve such an elastic force (i.e., friction force), the materials of the barrel 12 and the stoppers 16d, the shape of the stoppers 16d, etc. are appropriately selected.

According to the stoppers 16d as described above, the plunger 16 can be prevented from coming off from the barrel 12 without disposing a convex portion on the inner circumferential surface 12e of the barrel 12. Therefore, when the movable body 14 is housed into the barrel 12, the seal body 14b is not damaged by the convex portion disposed on the inner circumferential surface 12e.

According to the stoppers 16d as described above, the plunger 16 can be anchored at an arbitrary position on the inner circumferential surface 12e of the barrel 12. As a result, the injector 10 can have high usability.

Furthermore, in the case of the first embodiment, the two stoppers 16d are arranged oppositely to each other across the central axis C3 of the plunger 16, so that the central axis C3 of the plunger 16 can be aligned with the central axis C1 of the barrel 12.

Although the free ends 16f of the stoppers 16d are in elastic contact with the inner circumferential surface 12e of the barrel 12, if the user moves the plunger 16 backward, the free end 16f slides on the inner circumferential surface 12e, and the plunger 16 finally conies off from the barrel 12. To deal with such coming-off due to the user, as shown in FIG. 4, the circumferential groove 12f is formed in a portion near the base end 12b in the inner circumferential surface 12e of the barrel 12. The free ends 16f of the stoppers 16d engage with (fall and fit into) the circumferential groove 12f, so that the plunger 16 is restricted from moving toward the base end side of the barrel 12, and as a result, the plunger 16 is prevented from coming off from the barrel 12.

When the plunger 16 is housed into the barrel 12, the free ends 16f of the stoppers 16d may be caught in the circumferential groove 12f, which possibly makes it unable to smoothly move the plunger 16 toward the leading end 12a of the barrel 12. As a countermeasure, as shown in FIG. 4, the circumferential groove 12f includes a slope surface 12g extending from a bottom potion thereof toward the leading end 12a of the barrel 12 and sloping with respect to the inner circumferential surface 12e. Due to the slope surface 12g, the free end 16f falling into the circumferential groove 12f can return onto the inner circumferential surface 12e. As a result, the free ends 16f of the stoppers 16d can pass through the circumferential groove 12f without being caught.

When the movable body 14 is housed into the barrel 12, the slope surface 12g can also prevent the seal body 14b of the movable body 14 from being caught in the circumferential groove 12f. As a result, the seal body 14b can be prevented from being damaged by the circumferential groove 12f.

While describing the operation of the injector 10 according to the first embodiment, other features of the injector 10 will hereinafter be described with reference to FIGS. 8A to 8D.

Figure 8A:
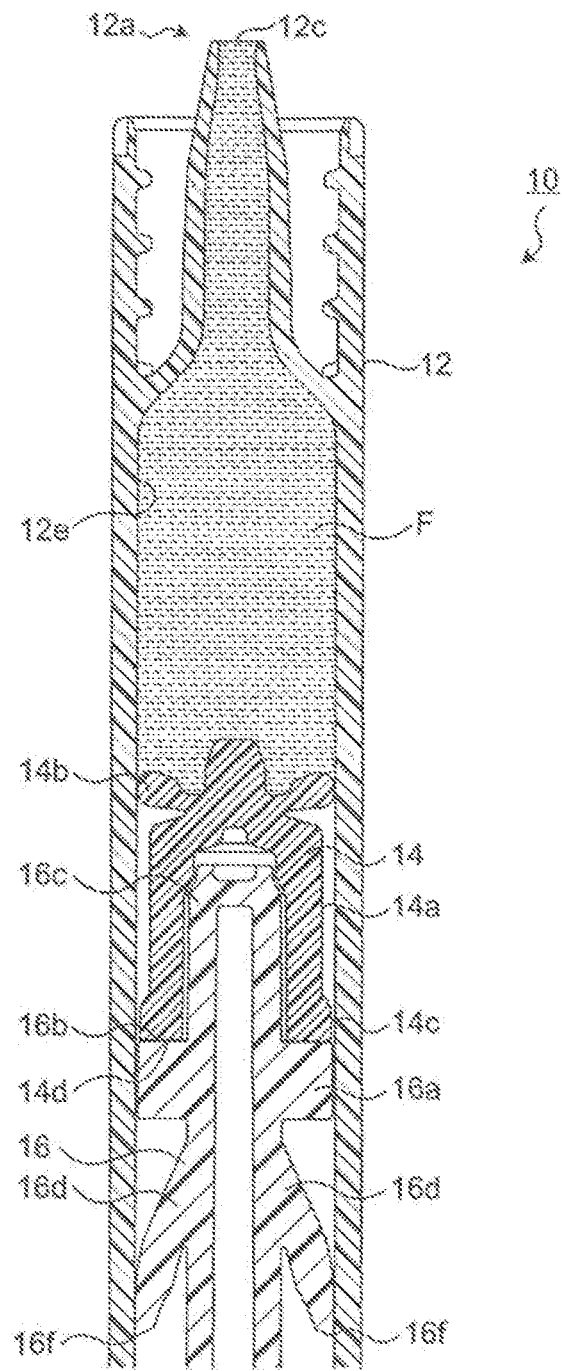
FIG. 8A is an enlarged cross-sectional view of the barrel while the plunger and the movable body are stopped.

FIG. 8A is an enlarged cross-sectional view of the barrel while the plunger and the movable body are stopped.

As shown in FIG. 8A, the seal body 14b of the movable body 14 is in close fluid-tight contact with the inner circumferential surface 12e of the barrel 12, so that a fluid F is contained in the barrel 12 without leaking from the base end side of the barrel 12 to the outside.

Figure 8B:
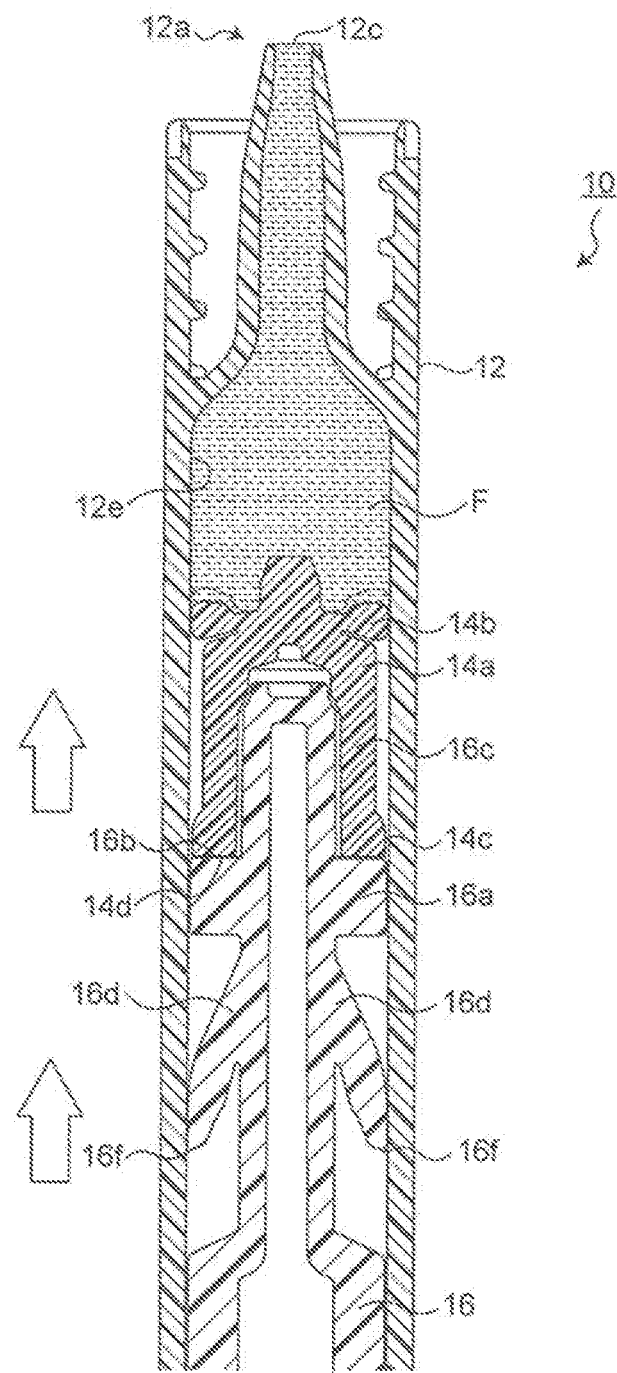
FIG. 8B is an enlarged cross-sectional view of the barrel during movement of the plunger and the movable body toward a leading end of the barrel.

FIG. 8B is an enlarged cross-sectional view of the barrel during movement of the plunger and the movable body toward the leading end of the barrel.

As shown in FIG. 8B, while the rear end surface 14d of the movable body 14 and the contact surface 16b of the plunger 16 are in contact with each other, the movable body 14 is pushed and moved toward the leading end 12a of the barrel 12 by the plunger 16. During movement of the movable body 14, the seal body 14b is elastically deformed. Specifically, due to the friction force generated between the outer circumferential end of the seal body 14b and the inner circumferential surface 12e of the barrel 12, the seal body 14b is elastically deformed such that the outer circumferential side portion of the seal body 14b approaches the main body 14a. The seal body 14b moves in this elastically deformed state and pushes and moves the fluid F toward the discharge port 12c.

Figure 8C:
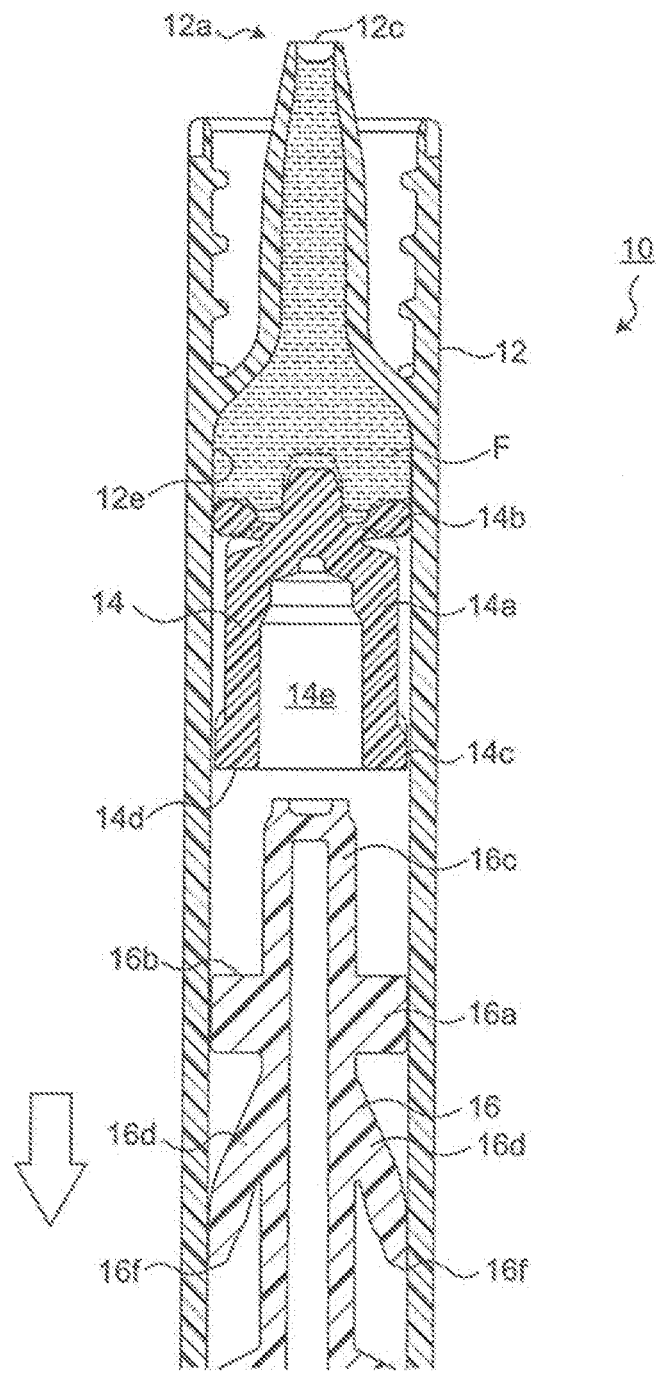
FIG. 8C is an enlarged cross-sectional view of the barrel during movement of the plunger in a direction away from the movable body.

FIG. 8C is an enlarged cross-sectional view of the barrel during movement of the plunger in a direction away from the movable body.

As shown in FIG. 8C, when the plunger 16 moves in a direction away from the movable body 14, i.e., toward the base end of the barrel 12, the movable body 14 is separated from the plunger 16 and stops in the barrel 12 in this state.

Immediately after the movable body 14 stops, as shown in FIG. 8A, the seal body 14b is returned (restored) to the original shape with the outer circumferential side portion separated from the main body 14a. In this case, the movable body 14 entirely retracts toward the base end of the barrel 12 without changing the contact position on the inner circumferential surface 12e of the barrel 12 in contact with the outer circumferential end of the seal body 14b. As a result, the fluid F in the nozzle tip 18 is drawn toward the seal body 14b, and the subsequent dripping of the fluid F is suppressed.

To allow the movable body 14 to retract toward the base end of the barrel 12 through the restoration of the seal body 14b without changing the position of contact of the seal body 14b with the barrel 12, the plunger 16 needs to retreat at the same time. In other words, a restoring force of the seal body 14b needs to exceed the friction force between the free ends 16f of the stoppers 16d of the plunger 16 and the inner circumferential surface 12e of the barrel 12. For this purpose, the material of the seal body 14b, the shape of the seal body 14b, etc. are appropriately selected.

When the movable body 14 retracts through the restoration of the seal body 14b without changing the position of contact of the seal body 14b with the barrel 12 as described above, the flange 14c is moved along the inner circumferential surface 12e of the barrel 12. As a result, the movable body 14 can retreat in the extending direction of the central axis C1 of the barrel 12. If the flange 14c does not exit, the movable body 14 retracts in a direction tilted with respect to the central axis C1 of the barrel 12, so that the movable body 14 may have a posture in which a portion of an outer edge of the rear end surface 14d comes into contact with the inner circumferential surface 12e of the barrel 12, i.e., a tilted posture. If the movable body 14 is tilted, the adhesion between the seal body 14b and the inner circumferential surface 12e of the barrel 12 is partially weakened, so that the fluid F may leak to the base end side of the barrel 12.

In the case of the first embodiment, the outer diameter d4 of the flange 14c of the movable body 14 is smaller than the inner diameter d1 of the barrel 12. Therefore, the flange 14c can be moved without strong contact with the inner circumferential surface 12e of the barrel 12, i.e., in a state of substantially zero friction force. Alternatively, the outer diameter d4 of the flange 14c of the movable body 14 may be equal to or larger than the inner diameter d1 of the barrel 12. However, the friction force between the flange 14c and the barrel 12 must be smaller than the friction force between the seal body 14b and the barrel 12. Otherwise, the restoration of the seal body 14b and the retraction of the movable body 14 due to the restoration cannot be achieved.

In the case of the first embodiment, as shown in FIG. 6, the distance L2 between the seal body 14b and the flange 14c in the movable body 14 is made larger than the outer diameter d3 of the seal body 14b. Therefore, when the movable body 14 retracts due to the restoration of the seal body 14b, the movable body 14 is hardly tilted (as compared to when the distance L2 is smaller than the outer diameter d3).

As shown in FIG. 8C, the plunger 16 separated from the movable body 14 is kept housed in the barrel 12 by the stoppers 16d without coming off from the barrel 12.

Figure 8D:
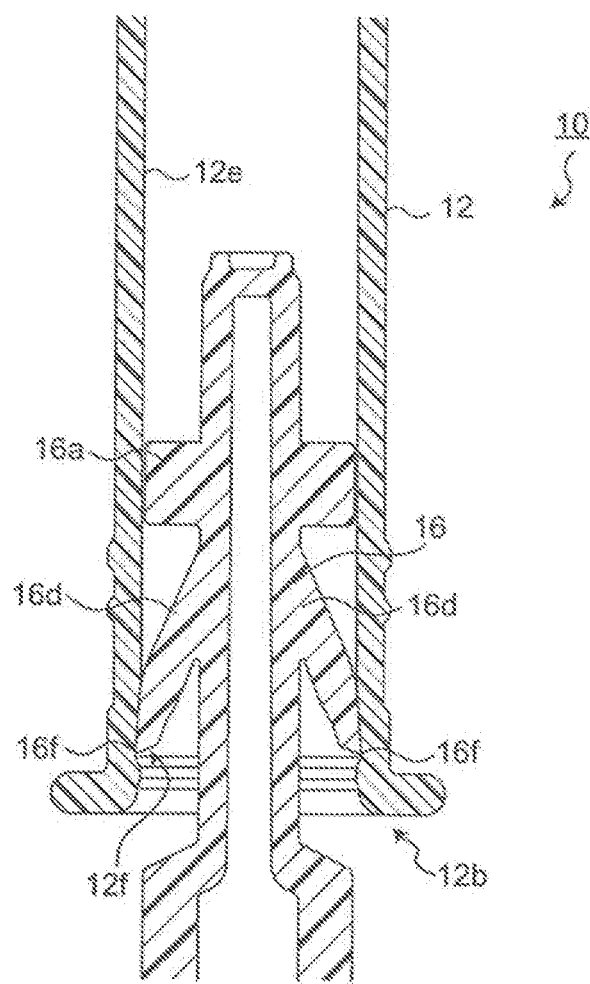
FIG. 8D is an enlarged cross-sectional view of the barrel while the plunger restricted from coming off from the barrel by a circumferential groove.

FIG. 8D is a partially enlarged cross-sectional view of the barrel while the plunger is restricted from coming off from the barrel by the circumferential groove.

As shown in FIG. 8D, the plunger 16 during retraction toward the base end of the barrel 12 due to pulling by the user is restrained by engagement of the free ends 16f of the stoppers 16d with the circumferential groove 12f. As a result, the plunger 16 is prevented from coming off from the barrel 12.

According to the first embodiment as described above, the seal body can be housed into the barrel without damage and the plunger can be prevented from falling off from the barrel in the injector.

Second Embodiment

A second embodiment is substantially the same as the first embodiment as descried above except that the form of the stoppers disposed on the plunger is different. Therefore, the second embodiment will be described mainly in terms of different points. The same reference numerals are given to constituent elements in the second embodiment that are substantially the same as the constituent elements in the first embodiment described above.

Figure 9:
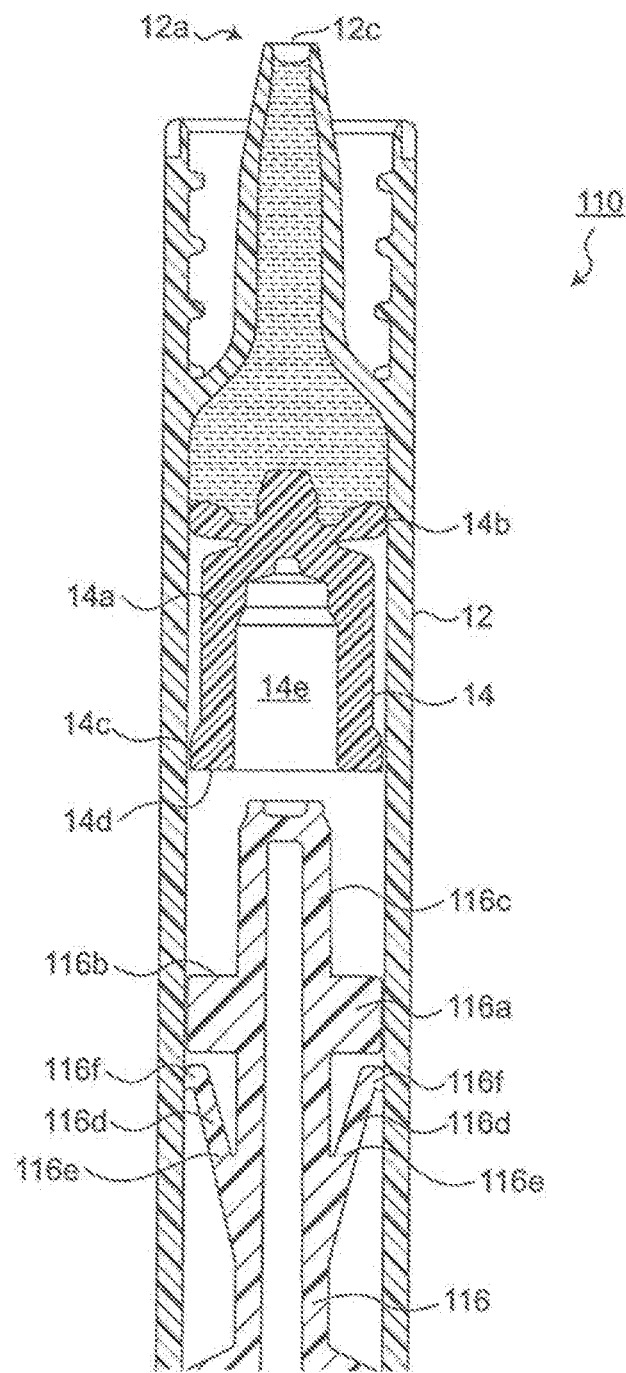
FIG. 9 is an enlarged cross-sectional view of a leading end portion of a barrel in an injector according to a second embodiment of the present invention.
Figure 10:
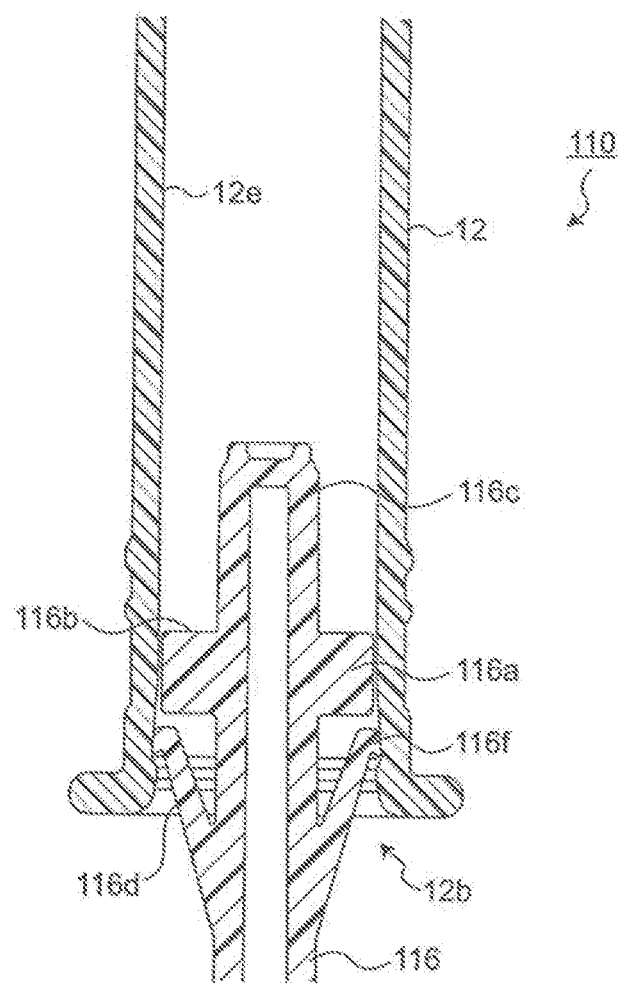
FIG. 10 is an enlarged cross-sectional view of a base end side portion of the barrel in the injector according to the second embodiment.

FIG. 9 is an enlarged cross-sectional view of a leading end side portion of a barrel in an injector according to the second embodiment. FIG. 10 is an enlarged cross-sectional view of a base end side portion of the barrel.

As shown in FIG. 9, in an injector 110 according to the second embodiment, a plunger 116 includes stoppers 116d. Each of the stoppers 116d is a plate spring-shaped member including a fixed end 116e attached to the plunger 116 and a free end 116f elastically contacting the inner circumferential surface 12e of the barrel 12.

In the case of the second embodiment, unlike the stopper 16d of the first embodiment, the free end 116f of the stopper 116d is located on the leading end side of the barrel 12 with respect to the fixed end 116e. Therefore, a contact surface 116b of the plunger 116 coming into contact with the rear end surface 14d of the movable body 14 is closer to the free end 116f of the stopper 116d as compared to the first embodiment shown in FIG. 8D.

Thus, as shown in FIG. 10, when the free end 116f of the stopper 116d is engaged with the circumferential groove of the barrel 12, the contact surface 116b of the plunger 116 is located closer to the base end 12b of the barrel 12. In other words, the movable body 14 having the rear end surface 14d brought into contact with the contact surface 116b is also disposed closer to the base end 12b of the barrel 12. As a result, a larger amount of the fluid can be contained in the barrel 12.

In the second embodiment as described above, as with the first embodiment, the seal body can be housed into the barrel without damage and the plunger can be prevented from falling off from the barrel in the injector.

Third Embodiment

In the case of the first embodiment described above, the stoppers preventing the plunger from coming off from the barrel are disposed on the plunger. In contrast, in the case of a third embodiment, stoppers are disposed on the barrel. Therefore, the third embodiment will be described mainly in terms of the different stoppers. The same reference numerals are given to constituent dements in the third embodiment that are substantially the same as the constituent elements in the first embodiment described above.

Figure 11:
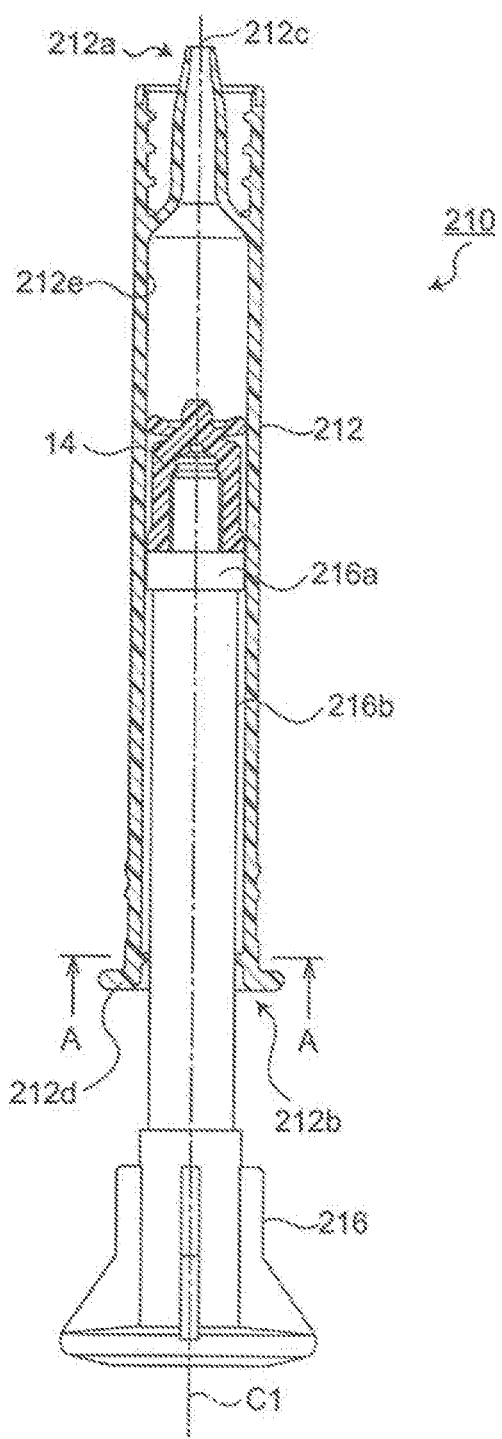
FIG. 11 is a partial cross-sectional view of an injector according to a third embodiment of the present invention.
Figure 12:
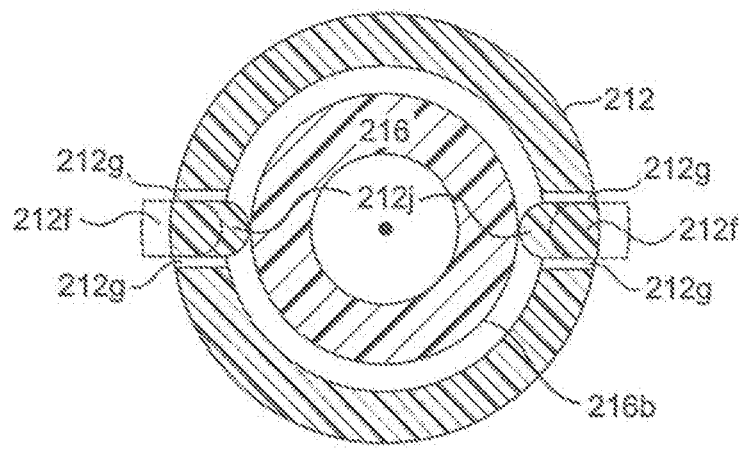
FIG. 12 is a cross-sectional view of the injector taken along a line A-A shown in FIG. 11.
Figure 13:
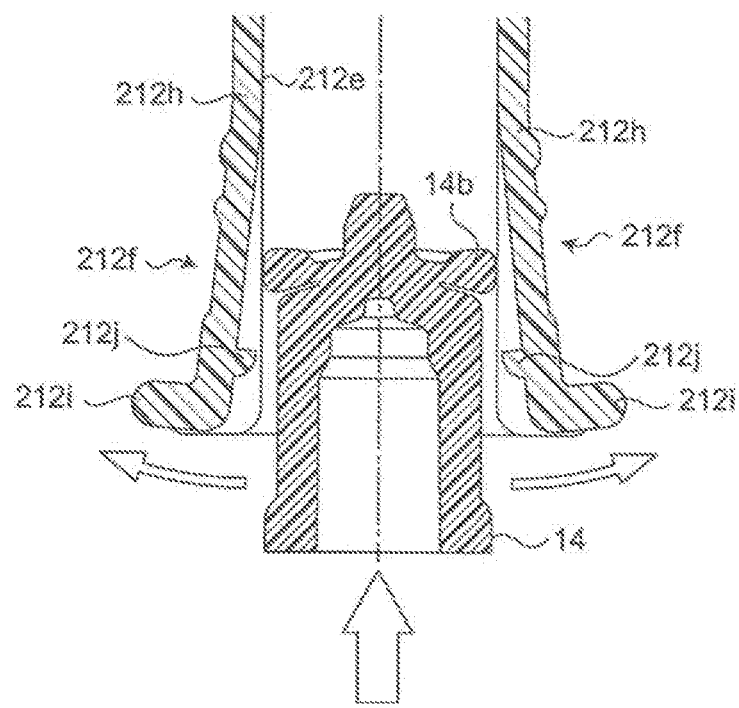
FIG. 13 is an enlarged cross-sectional view of a barrel, showing stoppers when the movable body is housed in the barrel.

FIG. 11 is a partial cross-sectional view of an injector according to the third embodiment, FIG. 12 is a cross-sectional view of the injector taken along a line A-A shown in FIG. 11. FIG. 13 is an enlarged cross-sectional view of a barrel, showing stoppers when the movable body is housed into the barrel. In FIG. 11, the nozzle tip and the finger grip are not shown.

As shown in FIGS. 11 and 2, in an injector 210 according to the third embodiment, no stopper is disposed on a plunger 216. Instead, as shown in FIG. 12, a pair of stoppers 212f facing each other is disposed on a barrel 212.

Specifically, in the case of the third embodiment, the stoppers 212f are made up of portions of the barrel 212 each interposed between two slits 212g formed to extend from a base end 212b of the barrel 212, As a result, a portion of the barrel 212 interposed between base portions of the two slits 212g is defined as a fixed end 212h of the stopper 212f. A claw 212j brought into elastic contact with the plunger 216 is disposed on the inner side of a free end 212i of each of the paired stoppers 212f. Therefore, the stopper 212f is a plate spring-shaped member (a plate spring-shaped member integrated with the barrel 212) having the fixed end 212h attached to the barrel 212 and the free end 212i brought into elastic contact with the plunger 216 (via the claws 212j).

A distance between the claws 212j of the pair of the stoppers 212f is made smaller than an outer diameter of a shaft portion 216b of the plunger 216. As a result, the pair of the claws 212j holds the shaft portion 216b of the plunger 216. Consequently, the plunger 216 is prevented from coming off from the barrel 212.

The planer 216 during retraction toward the base end 212b of the, barrel 212 due to pulling by the user is restrained when a contact portion 216a for contact with the movable body 14 is brought into contact with the claws 212j. As a result, the plunger 216 is prevented from coming off from the barrel 212.

As shown in FIG. 13, when the movable body 14 is housed into the barrel 212, the pair of the stoppers 212f is elastically deformed such that the free ends 212i move away from each other. As a result, the movable body 14 can be housed into the barrel 212 without bringing the claws 212j of the stoppers 212f into contact with the seal body 14b.

In the third embodiment as described above, as with the first embodiment, the seal body can be housed into the barrel without damage and the plunger can be prevented from falling off from the barrel in the injector.

Although the present invention has been described with three embodiments, the present invention is not limited to these embodiments.

For example, in the case of the first embodiment described above, the seal body 14b and the plunger 16 are separate parts; however, the embodiments of the present invention are not limited thereto. The seal body and the plunger may be integrated as one part.

Therefore, in a broad sense, the injector according to the embodiment of the present invention is an injector comprising a cylindrical barrel including a discharge port, a seal body coming into close contact with an inner circumferential surface of the barrel, a plunger for pushing and moving the seal body to the discharge port side of the barrel, and a stopper disposed on one of the barrel and the plunger and coming into elastic contact with the other in a radial direction of the barrel.

INDUSTRIAL APPLICABILITY

The present invention is applicable to any injector for injecting a fluid.

EXPLANATIONS OF LETTERS OR NUMERALS 10 injector
12 barrel
12e inner circumferential surface
14b seal body
16 plunger
16d stopper

What is claimed is:
1. An injector comprising:
   a cylindrical barrel including a leading end having a discharge port and a base end;
   a seal body coming into close contact with an inner circumferential surface of the cylindrical barrel;
   a plunger for pushing and moving the seal body to a discharge port side of the cylindrical barrel; and
   a stopper disposed on the plunger in a non-separable manner and coming into elastic contact with the cylindrical barrel in a radial direction of the cylindrical barrel between the leading end and the base end of the cylindrical barrel,
   wherein the stopper has a fixed end attached to the plunger and a free end in contact with the cylindrical barrel, and
   wherein the stopper extends from the fixed end to the free end both in the radial direction of the cylindrical barrel and in a direction toward the base end of the cylindrical barrel, and
   wherein the seal body and the plunger are configured to separate from each other by retracting the plunger.

2. The injector according to claim 1, wherein the stopper is a plate spring-shaped member including the fixed end attached to the plunger and the free end coming into elastic contact with the inner circumferential surface of the cylindrical barrel.

3. The injector according to claim 2, wherein the inner circumferential surface of the cylindrical barrel is provided with a circumferential groove with which the free end of the stopper is engagable.

4. The injector according to claim 3, wherein the circumferential groove has a slope surface extending from a bottom portion of the circumferential groove toward the leading end of the cylindrical barrel and sloping with respect to the inner circumferential surface.

5. The injector according to claim 2, wherein the stopper and the plunger are integrated as one part.

6. An injector comprising:
   a cylindrical barrel including a leading end having a discharge port and a base end;

a seal body coming into close contact with an inner circumferential surface of the cylindrical barrel;

a plunger for pushing and moving the seal body to a discharge port side of the cylindrical barrel; and a stopper disposed on the plunger and coming into elastic contact with the cylindrical barrel in a radial direction of the cylindrical barrel between the leading end and the base end of the cylindrical barrel, wherein the stopper has a fixed end attached to the plunger and a free end in contact with the cylindrical barrel, and wherein the stopper permanently extends from the fixed end to the free end both in the radial direction of the cylindrical barrel and in a direction toward the leading end of the cylindrical barrel.

7. The injector according to claim 6, wherein the stopper is a plate spring-shaped member including the fixed end attached to the plunger and the free end coming into elastic contact with the inner circumferential surface of the cylindrical barrel.

8. The injector according to claim 7, wherein the inner circumferential surface of the cylindrical barrel is provided with a circumferential groove with which the free end of the stopper is engagable.

9. The injector according to claim 8, wherein the circumferential groove has a slope surface extending from a bottom portion of the circumferential groove toward the leading end of the cylindrical barrel and sloping with respect to the inner circumferential surface.

10. The injector according to claim 7, wherein the stopper and the plunger are integrated as one part.

11. The injector according to claim 6, wherein the seal body and the plunger are integrated as one part.

12. The injector according to claim 1, wherein the fixed end of the stopper is rigidly attached to the plunger.

* * * * *